United States Patent
Räther et al.

(10) Patent No.: US 9,546,980 B1
(45) Date of Patent: Jan. 17, 2017

(54) SPATIAL ZOOM MODE FOR ACCUMULATIVE TRAPPED ION MOBILITY SPECTROMETRY

(71) Applicant: Bruker Daltonik GmbH, Bremen (DE)

(72) Inventors: Oliver Räther, Lilienthal (DE); Melvin Andrew Park, Billerica, MA (US)

(*) Notice: Subject to any disclaimer, the term of this patent is extended or adjusted under 35 U.S.C. 154(b) by 0 days.

(21) Appl. No.: 14/931,125

(22) Filed: Nov. 3, 2015

(51) Int. Cl.
*H01J 49/00* (2006.01)
*G01N 27/62* (2006.01)
*H01J 49/04* (2006.01)

(52) U.S. Cl.
CPC .......... *G01N 27/622* (2013.01); *H01J 49/004* (2013.01); *H01J 49/0404* (2013.01)

(58) Field of Classification Search
CPC .... G01N 27/622; H01J 49/004; H01J 49/0404
USPC ................ 250/281, 282, 286, 288
See application file for complete search history.

(56) References Cited

U.S. PATENT DOCUMENTS

| 5,736,740 A | 4/1998 | Franzen |
| 7,838,826 B1 | 11/2010 | Park |
| 8,766,176 B2 | 7/2014 | Park |
| 2016/0231275 A1* | 8/2016 | Park .................... G01N 27/622 |

* cited by examiner

*Primary Examiner* — Michael Maskell
(74) *Attorney, Agent, or Firm* — Benoit & Cote, Inc.

(57) ABSTRACT

The invention relates to the operation of ion mobility spectrometers based on gases pushing the ions over electrical field barriers, preferably in combination with mass spectrometers, and relates to trapped ion mobility spectrometers ("TIMS"). The invention proposes to accumulate and to scan the ions of a selected range of mobilities by using a long and flat electric field ramp created by additional voltages. By a voltage supplied at the beginning of the flat ramp, the lowest mobility of the mobility range of ions to be collected can be selected. By the difference of the voltages at the beginning and the end, the width of the mobility range is determined. The spatial zoom advantageously can collect considerable more ions of interest than a temporal zoom without severe losses by space charge effects, and more ions can be detected in the mass-mobility map.

13 Claims, 6 Drawing Sheets

SPATIAL ZOOM MODE FOR ACCUMULATIVE TRAPPED ION MOBILITY SPECTROMETRY

BACKGROUND OF THE INVENTION

Field of the Invention

The invention relates to methods and devices for the highly sensitive acquisition of high resolution ion mobility spectra.

Description of the Related Art

In document U.S. Pat. No. 7,838,826 B1 (M. A. Park, 2008), a small ion mobility spectrometer is presented. The length of the essential ion mobility scanning part, the ion mobility scanning tunnel, amounts to about five centimeters only; with additional entrance and exit funnels the device is less than ten centimeters long. The cylindrical ion mobility scanning tunnel comprises a quadrupolar RF field keeping the ions near the axis; separation of ions according to their mobilities is based upon a gas flow in the tunnel, driving the ions in an accumulation phase from an ion source against a ramp of an electric DC counter-field barrier. After shutting down the delivery of further ions, a scan phase starts, in which the field barrier is steadily decreased. Ions are driven in this scan phase by the gas flow over the decreasing top of the field barrier, thereby releasing successively ions from low mobilities to higher and higher mobilities from being trapped by the barrier. The ions can be detected in an ion detector, resulting in a mobility spectrum. Particularly, the ions may be measured by a mass spectrometer, e.g. a time-of-flight mass spectrometer, resulting in a two-dimensional mass-mobility map. The advantage of this tiny mobility spectrometer over all other mobility spectrometers is the possibility to choose a wanted mobility resolution by choosing the right scan speed. With extremely low scan speeds, the device by M. A. Park has already achieved ion mobility resolutions up to $R_{mob}=400$, a very high ion mobility resolution never achieved by any other mobility spectrometer. The device became widely known as "TIMS", "trapped ion mobility spectrometer". The principle of the device and its basic operation is outlined in FIG. 1.

In FIG. 2, the ion mobility resolution of this instrument is plotted as function of the time needed for a scan over the usual range of ion mobilities. With a scan time of only 20 milliseconds, a mobility resolution of about $R_{mob}=60$ is achieved, with 300 milliseconds scan time, the resolution amounts to $R_{mob}=120$.

The document U.S. Pat. No. 8,766,176 B2 ("Acquisition Modes for Ion Mobility Spectrometers using Trapped Ions", D. A. Kaplan et al.; 2011) presents a variety of scan modes for TIMS, e.g. a scan mode to achieve a linear mobility scale. A special scan mode concerns a "temporal zoom mode", wherein the scan runs with high speed through a first range of ions with low mobilities, more or less to get rid of the ions, traverses a second range of mobilities with low speed to measure the mobilities of the ions in this range with high ion mobility resolution, and passes through the end of the mobility spectrum with high speed again. This procedure saves time, if only a small range of mobilities is to be measured with highest mobility resolution. Such a temporal zoom mode is not achievable with drift tubes or any other type of mobility spectrometers.

U.S. patent application Ser. No. 14/614,463 ("High Ion Utilization Ion Mobility Separator for Mass Spectrometers", M. A. Park and O. Räther) illustrates how the influence of space charge in selected mobility ranges can be diminished by flattening the ramp of the electric barrier. If the ramp is made flatter in a certain range of the mobility spectrum, the ion clouds of different mobilities within this range are spatially uncompressed, reducing the influence of space charge causing ion losses due to Coulomb forces. The effect of non-linear electric field ramps on the density of accumulated ions is illustrated in FIG. 3 showing a decompression of high mass ions (low mobility). High mass ions are highly endangered to be piled out of the tunnel by space charge forces because they are only weakly bound inside the tunnel by the quadrupolar RF field. Experiments proved that losses of heavy ions of interest are greatly diminished.

U.S. patent application Ser. No. 14/614,456 ("Trapping Ion Mobility Spectrometer with Parallel Accumulation", M. A. Park and M. Schubert) presents an ion mobility spectrometer of the type described in the various documents cited above, additionally equipped with an extra upfront accumulation unit, the accumulation unit having the same form as the scanning unit. The accumulation unit operates in parallel with the scan by the separator tunnel. That is, while the separator is being used to analyze the mobilities of a first group of ions, the accumulation unit is simultaneously collecting a second group of ions from an ion source. This second group of ions is then rapidly transferred—in about a millisecond—to the ion mobility scanning tunnel once the analysis of the first group is complete. This allows the ion accumulation unit to collect ions nearly continuously while the separator tunnel analyzes ions nearly continuously in a repetitive way. The utility rate of ions generated in the ion source and transferred into the vacuum system is nearly 100 percent. An example of the device with an ion accumulation tunnel and an ion mobility scanning tunnel and its operation is shown in FIG. 4. In both the ion accumulation tunnel and the ion mobility scanning tunnel, the ions are gathered on an electric field ramps, separating the ions according to their mobility and diminishing the deteriorating effect of space charge on the ion collection causing ion losses.

There is still a need for devices and methods for the acquisition of mass-mobility maps with highest utility rates of the ions generated in an ion source of a mass spectrometer, with range of ion mobilities, mobility separation time and mobility resolution adaptable to the requirements of a given analytical task.

SUMMARY OF THE INVENTION

The invention uses the "TIMS" ion mobility spectrometer described in U.S. Pat. No. 7,838,826 B1; favorably in an embodiment using TIMS with parallel accumulation as described in document U.S. Ser. No. 14/614,456 equipped with an ion accumulation tunnel and an ion mobility scanning tunnel.

The invention basically proposes to accumulate and to scan the ions of a selected range of mobilities only by using a long and flat electric field ramp in the ion mobility scanning tunnel. The flat field ramp is extended to almost the complete length of the tunnel. The flat field ramp is created by adjustable voltages at electrodes near the beginning and the end of the ion mobility scanning tunnel. In TIMS, the voltages for the electric field ramp along the electrodes can be delivered by a special voltage divider, the resistances of which increase by R, R+ΔR, R+2ΔR, R+3ΔR, R+4ΔR, and so on, to create a linear increase of the electric field. If two points of the chain of electrodes are supplied with two adjustable voltages, a linear field gradient along the electrodes between these points is maintained for all pairs of voltages.

By the voltage supplied at the beginning of the flat ramp, the lowest mobility of the mobility range of ions to be collected can be selected. By the difference of the voltages at the beginning and the end, the width of the mobility range is determined. If the full range of mobilities has to be measured, this full range may be divided into three, four, five, or more sections, and the mobility of the ions within these sections may be measured one after the other with high mobility resolution and high sensitivity.

If the favorable embodiment of TIMS with parallel accumulation is used, similar field profiles are generated in the ion accumulation tunnel and in the ion mobility scanning tunnel. In the accumulation tunnel, a field peak at the end keeps ions with low mobility from entering the mobility scanning tunnel during scans. During transfer of the ions from the accumulation tunnel to the scanning tunnel, these ions of low mobility are not kept in the scanning tunnel, instead they pass this tunnel and are removed somewhere downstream.

In contrast to the "temporal zoom" described in U.S. Pat. No. 8,766,176 B2, the zoom according to this invention will be called "spatial zoom" because the zoom spreads the ions of the mobility range of interest over almost the full space of the ion mobility scanning tunnel. If additionally an accumulation tunnel is used, the ions of the mobility range of interest are likewise spread over almost the full space of this tunnel. The spatial zoom advantageously can collect considerably more ions of interest than the temporal zoom without severe losses by space charge effects, and more ions can be detected in the mass-mobility map.

The electric field at the ramp can also be generated by supplying multiple DC voltages to some or all electrodes wherein the multiple DC voltages are each generated by a separate, preferably programmable, DC voltage supply. If some, but not all, of the electrodes are connected to one of the separate DC voltage supplies, the electrodes can be connected by a chain of resistors. If all of the electrodes are connected to one of the separate DC voltage supplies, the electrodes are preferably electrically isolated from each other.

The rise of the electric field along the flat part of the electric field ramp is preferably adjusted such that ions of a limited mobility range are accumulated at the flat part before scanning the ramp. The limited mobility range is preferably between 5% to 30% of the mobility range of ions to be analyzed. The minimum and maximum of the flat electric field ramp can be adjusted in subsequent scans of the ramp in order to cover the whole mobility range wherein the rise of the electric field along the flat part does not need to be the same in each one of the scans. The flat part preferably extends spatially along more than 70%, and most preferably more than 90%, of the electric field ramp of the ion mobility scanning tunnel.

Because it is difficult to generate sharp kinks of the electric field strength along the axis of the device, special grids may be introduced at some positions. In order to keep the quadrupolar RF field intact, the grids should comprise filaments either made from leaky dielectric material, or the filaments should be inductive, e.g. by winding electrically conductive material around an insulating filament.

DETAILED DESCRIPTION

The invention is based upon the ion mobility spectrometer ("TIMS") presented in U.S. Pat. No. 7,838,826 B1, and particularly to the TIMS device with parallel accumulation as described in U.S. Ser. No. 14/614,456 and equipped with ion accumulation tunnel and ion mobility scanning tunnel.

Figure 6:
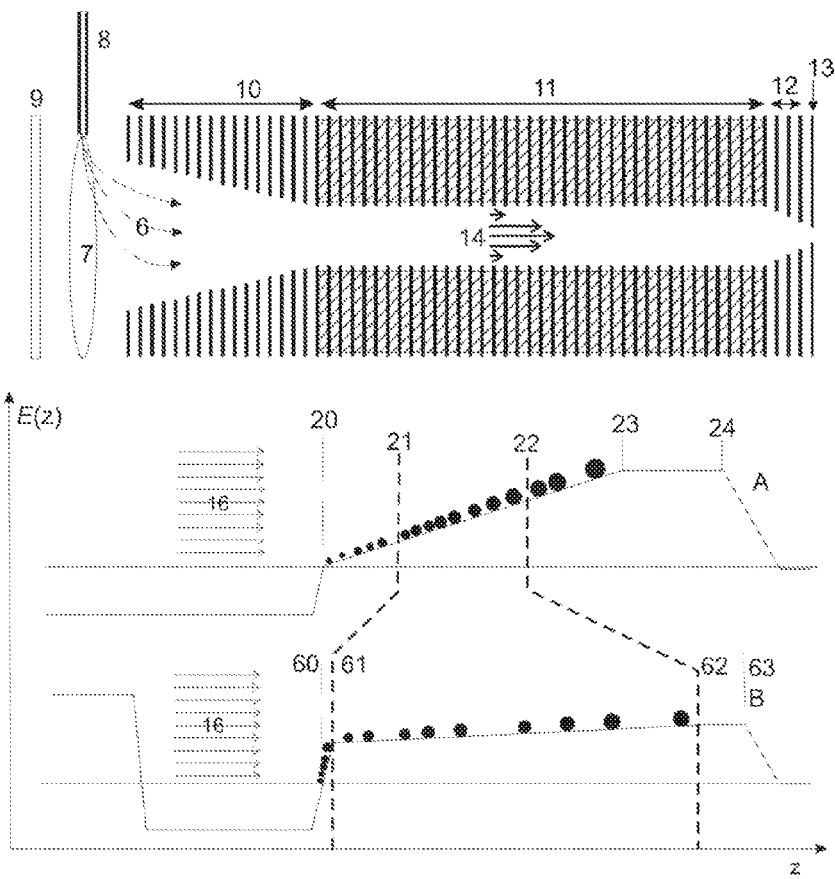
FIG. 6 presents the spatial zoom mode according to this invention. The diagram depicts two different profiles of the electric field. In the upper field profile (A), the electric field strength increases linearly between locations (20) and (23) along the axis z of the device. Below, in field profile (B), the ramp of the electric field shows that a very steep and narrow field gradient is positioned between z-locations (60) and (61), a wide and flat ramp is located between (61) and (62), and a plateau between z-locations (62) and (63). By adjustable DC voltages at z-locations (61) and (62), a range of ions with mobilities of interest can be selected. In this case, the ion clouds between positions (21) and (22) of profile (A) are accumulated on the flat ramp between location (61) and (62) of profile (B). The ion clouds accumulated on the flat ramp are uncompressed and experience low influence only of space charge forces. More ions can be collected in this range than with field profile (A) by longer accumulation times without severe losses of ions. The ions on the flat part of the ramp can then be measured with high mobility resolution. The operation needs a DC generator with two additional adjustable voltages to deliver the voltages supplied to the electrodes at locations (61) and (62).

As shown in the lower portion of FIG. 6, the invention involves applying additional voltages to the electrodes (61) and (62) near the ends of the TIMS ion mobility separation tunnel (11) in order to generate a long and flat electric field ramp on which ions of an interesting range of mobilities only can be accumulated for the ion mobility scan. The flat field ramp is extended to almost the complete length of the tunnel, decompressing the density of the ion clouds and diminishing the effect of space charge. More ions can be collected on the flat ramp without severe losses, and the ions can then be measured with preselected ion mobility resolution by choosing the right scan speed.

Only two additional voltages are needed for the invention. In the TIMS device, the voltages along the electrodes are delivered by a special voltage divider, the resistances of which increase by R, R+ΔR, R+2ΔR, R+3ΔR, R+4ΔR, and so on, to create a linear increase of the electric field. If two points of the chain of electrodes are supplied with two adjustable voltages, the linear field gradient along the electrodes is maintained for all pairs of voltages.

By the voltages supplied to the beginning (41) of the flat ramp, the highest mobility of the mobility range of interest can be selected. By the difference of the voltages at the beginning (41) and the end (42), the width of the mobility range between highest and lowest mobility of interest is determined. If the full range of mobilities has to be measured, the full range may be divided into three, four, five, or more sections, and the mobility of the ions within these sections may be measured one after the other with high mobility resolution and high sensitivity.

Figure 1:
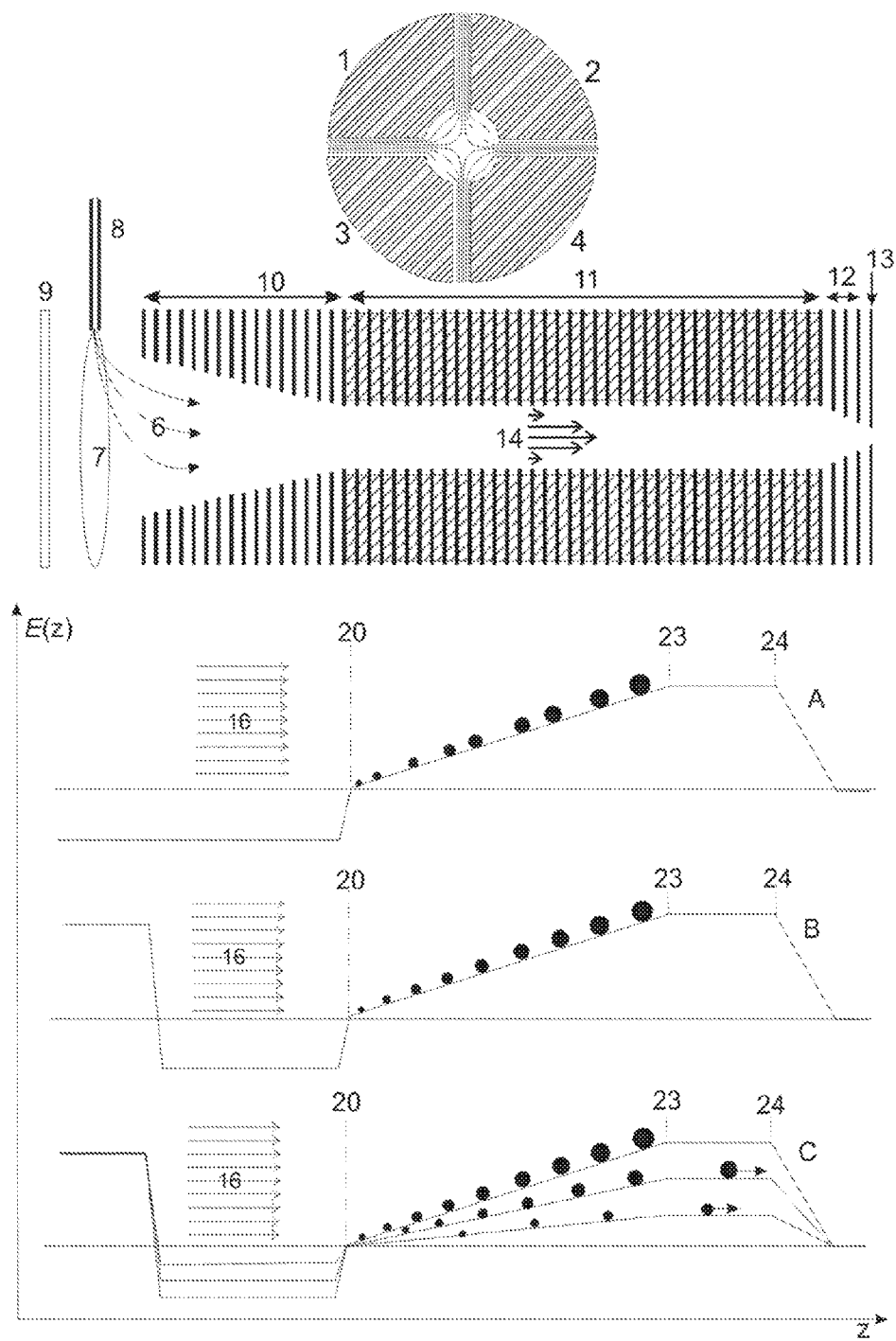
FIG. 1 schematically illustrates the design and operation of an ion mobility spectrometer according to the state of the art, as described in U.S. Pat. No. 7,838,826 B1 (M. A. Park, 2008). The ion mobility scanning tube (11) between entrance funnel (10) and exit funnel (12) amounts to only 48 millimeters in length; the inner diameter amounts to eight millimeters. The ion mobility scanning tube (11) consists of a series of segmented diaphragms with quadrant electrodes (1) to (4), to generate a quadrupolar RF field, as shown in the top of the figure. Ions (6) from an ion source (not shown) are introduced by capillary (8) together with a gas stream (7) into a first vacuum chamber. A repeller plate (9) directs the ions (6) into the funnel (10); the gas flow (14) drives the ions into the ion mobility scanning tube (11). In the three diagrams $E(z)=f(z)$ in the bottom part of the figure, z being the coordinate along the axis of the device, the electric field profiles are shown for three phases of operation: In the accumulation phase (A) ions are blown by the gas flow (14, 16) onto the rising edge ("ramp") of the electric field profile between z locations (20) and (23). In a short trap phase (B) of only one to two milliseconds after discontinuing further supply of ions, the ions assume their equilibrium states on the rising edge according to their mobility. The steadily decreasing profile voltage in the scan phase (C) releases ions in the order of increasing mobilities over the field plateau between locations (23) and (24) and through the exit funnel towards an ion detector. Ion current measurements versus time represent the ion mobility spectrum from low mobilities to high mobilities.
Figure 2:
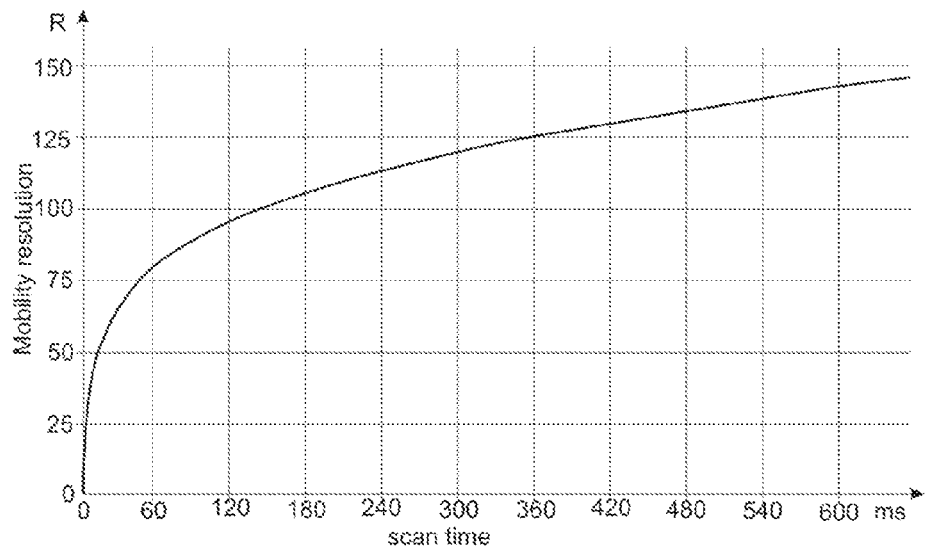
FIG. 2 presents the dependence of the achievable mobility resolution $R_{mob}$ for the device shown in FIG. 1, given for ions of low mobility ($K\approx0.5$ m$^2$/Vs), on the scan time $t_s$. The scan time $t_s$ encompasses the full scan from low mobilities ($K\approx0.5$ m$^2$/Vs) to high mobilities ($K\approx1.0$ m$^2$/Vs). Usually, the general interest is on ions of low mobility because they show the highest variety of folding states. A scan time of only 20 milliseconds over the full range of mobilities already achieves a mobility resolution of $R_{mob}\approx60$, whereas a mobility resolution of $R_{mob}\approx120$ needs a much longer scan time of 300 milliseconds.
Figure 3:
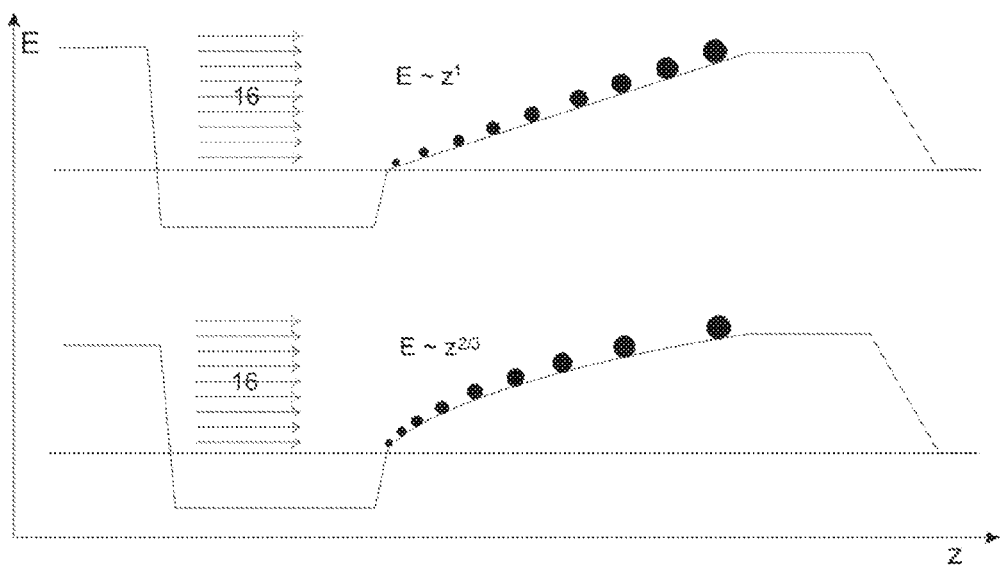
FIG. 3 presents two different profiles of the electric field, generating different ion densities near the top of the electric field profile, according to patent application U.S. Ser. No. 14/614,463 ("High Ion Utilization Ion Mobility Separator for Mass Spectrometers," M. A. Park and O. Räther). In the upper part, repeated from FIG. 1, the electric field strength increases linearly along the axis z of the device, showing equal ion density along the ramp, if a mixture of ions with evenly distributed mobilities is provided. In the bottom profile, the electric field increases proportionally to $Z^{2/3}$. As indicated by the dots, high mass ions near the top of the ramp are uncompressed by the field proportional to $z^{2/3}$, whereas low mass ions are compressed at the foot of the ramp. Near the top of the ramp, the space charge is diminished, and losses of high mass ions are considerably reduced.
Figure 4:
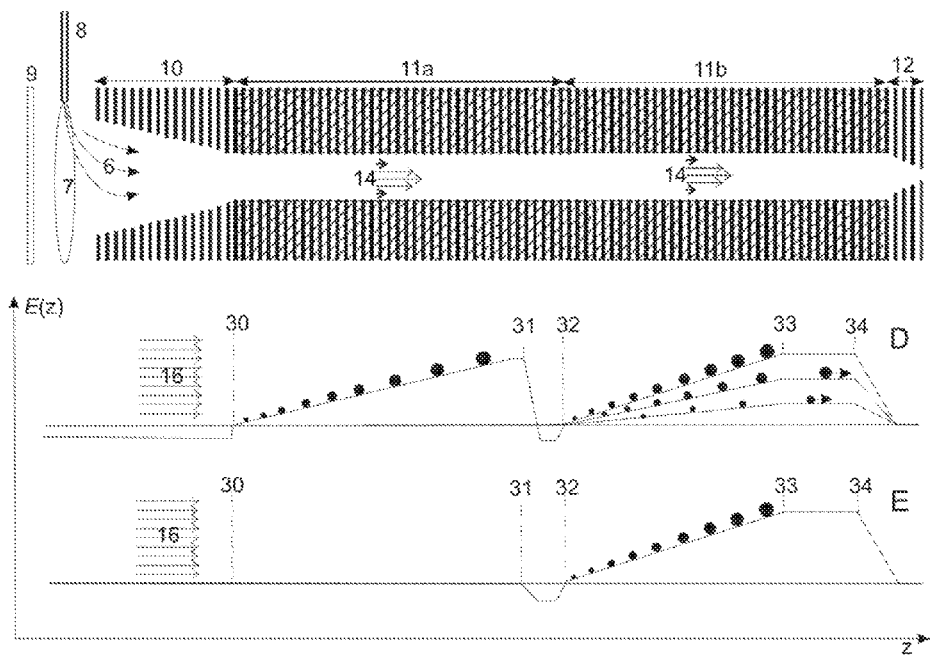
FIG. 4 depicts in its upper part schematically an embodiment of the mobility spectrometer presented in patent application U.S. Ser. No. 14/614,456 ("Trapping Ion Mobility Spectrometer with Parallel Accumulation", M. A. Park and M. Schubert). The spectrometer comprises an elongated tunnel (11), divided into an ion accumulation unit (11a) and an ion mobility scan unit (11b), an RF voltage supply unit (not shown) for RF voltages at the quadrants of the electrodes and DC voltage supply units (likewise not shown) for the electrodes of the two tunnel units, contacting the electrodes at locations (31) and (34). Chains of resistors between the diaphragms in both tunnel units produce the two field profiles, shown in diagram (D) below in the figure. The operation consists of two phases only: In the accumulation and scan phase (D), ions (6) from an ion source (not shown) are accumulated on the rising edge of the electric field profile in the accumulation unit (11*a*) of the tube whilst, at the same time, the ions are scanned according to their mobility by decreasing the voltage supplied to location (34) of the ion mobility scan unit (11*b*), thereby releasing the ions with higher and higher mobilities through the exit funnel (13) towards the ion detector. In the transfer phase (E), first the voltage for the scan unit (11*b*) is restored, and then the voltage of the accumulation unit (11*a*) is switched off to let the ions be blown by the gas flow (14, 16) onto the ramp of the electric field profile of the ion mobility scan unit (11*b*). The transfer is completed after only one millisecond, and the accumulation and scan phase may start again by switching on the voltage at location (31).
Figure 7:
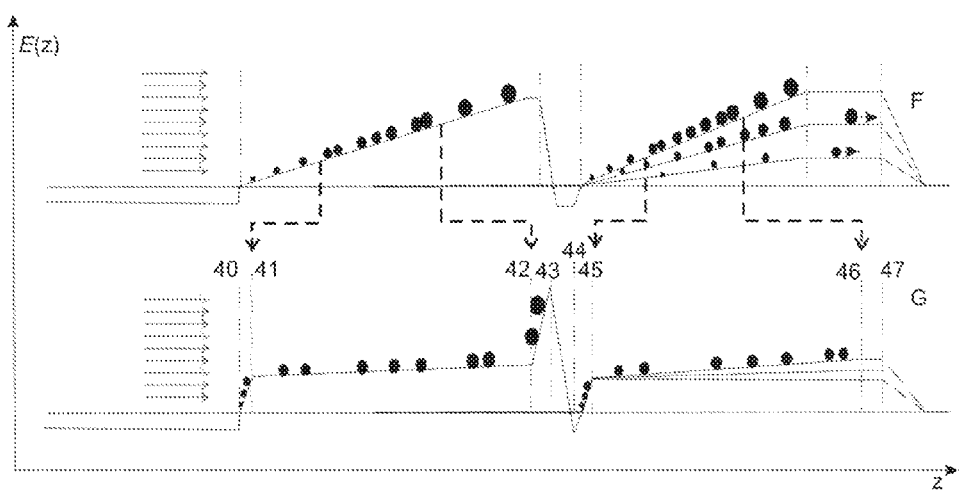
FIG. 7 presents the spatial zoom mode for the accumulative TIMS shown in FIG. 4 according to this invention. The diagram depicts two different profiles of the electric field. In the upper field profile (F), repeating the profile (D) of FIG. 4 for reasons of comparison, but with higher density of ions, the electric field strength increases linearly along the axis z of the device. Below, in field profile (G), the ramp of the electric field shows, in the accumulation unit as well as in the scan unit, three field gradients. In the accumulation profile, a very steep and narrow field gradient is positioned between z-locations (40) and (41), a wide and flat ramp is located between (41) and (42), and a further steep ramp is positioned between z-locations (42) and (43), forming a peak of the electric field strength. In the right-hand site scan profile, similar ranges with field gradients are positioned between z locations (44) and (45), and between (45) and (46). Between locations (46) and (47), the electric field peak is replaced by a plateau with constant field strength. By adjustable DC voltages supplied to electrodes at z-locations (41) and (42), a range of ions with mobilities of interest can be selected. The ions are accumulated on the flat ramp, uncompressed and with low influence of space charge forces. More ions can be collected in this range than with field profile (F) by longer accumulation times without severe losses of ions. After the scan phase is finished, the ions are transferred from the ion accumulation part to the ion mobility scanning part of the tube, whereby the ions collected at the ramp of the electric field peak between locations (42) and (43) pass the scan tube and are removed somewhere in the mass spectrometer. The ions on the flat part of the ramp can then be measured with high mobility resolution. The operation needs a DC generator with three additional adjustable voltages to deliver the voltages supplied to the electrodes at locations (41), (42), and (45). The electrodes at locations (45) and (47) are supplied with same voltages as the electrodes at locations (41) and (42) respectively. During the scan, the voltage at location (47) is continuously turned down.

The invention has particular advantages if it is applied to the accumulative TIMS device presented in FIG. 4. In FIG. 7, both the normal field profile (F) and the field profile (G) according to this invention are shown. The invention involves applying additional voltages to the electrodes near the ends (41) and (42) of the ion accumulation tunnel (11a) and at the beginning (45) of the ion mobility scanning tunnel (11b) in order to generate long and flat electric field ramps on which ions of an interesting range of mobilities can be accumulated and stored for the mobility scan. The flat field ramps are extended to almost the complete length of both tunnels (11a) and (11b). In the ion accumulation tunnel (11a), a field peak at the end with a steep ramp between locations (42) and (43) keeps ions with lowest mobility (of no interest) from entering the scanning tunnel during scans. During transfer of the ions from the accumulation tunnel to the scanning tunnel, these presently not interesting ions of lowest mobility are not kept in the ion mobility scanning tunnel, instead they pass the ion mobility scanning tunnel and are removed somewhere downstream from the mobility scanner.

Figure 5:
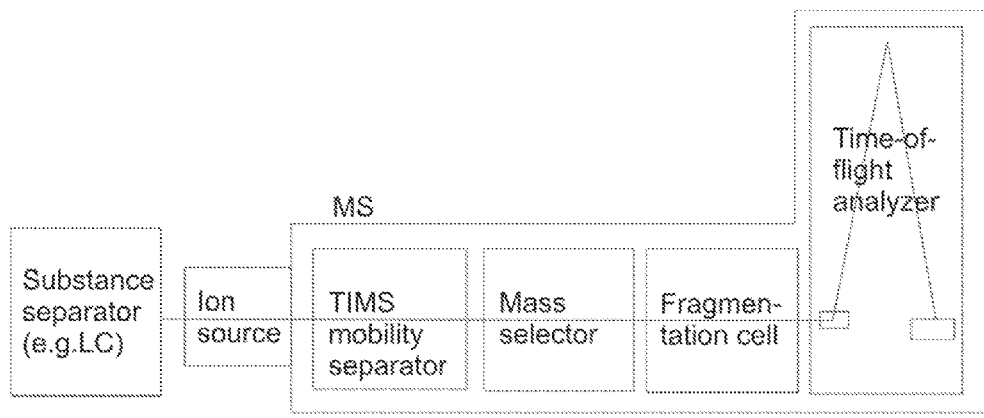
FIG. 5 shows a schematic overview of an LC-IMS-MS-MS mass spectrometer. This device can be used for an operation according to the invention, if additional DC voltages can be delivered by the inherent electronics.
Figure 8:
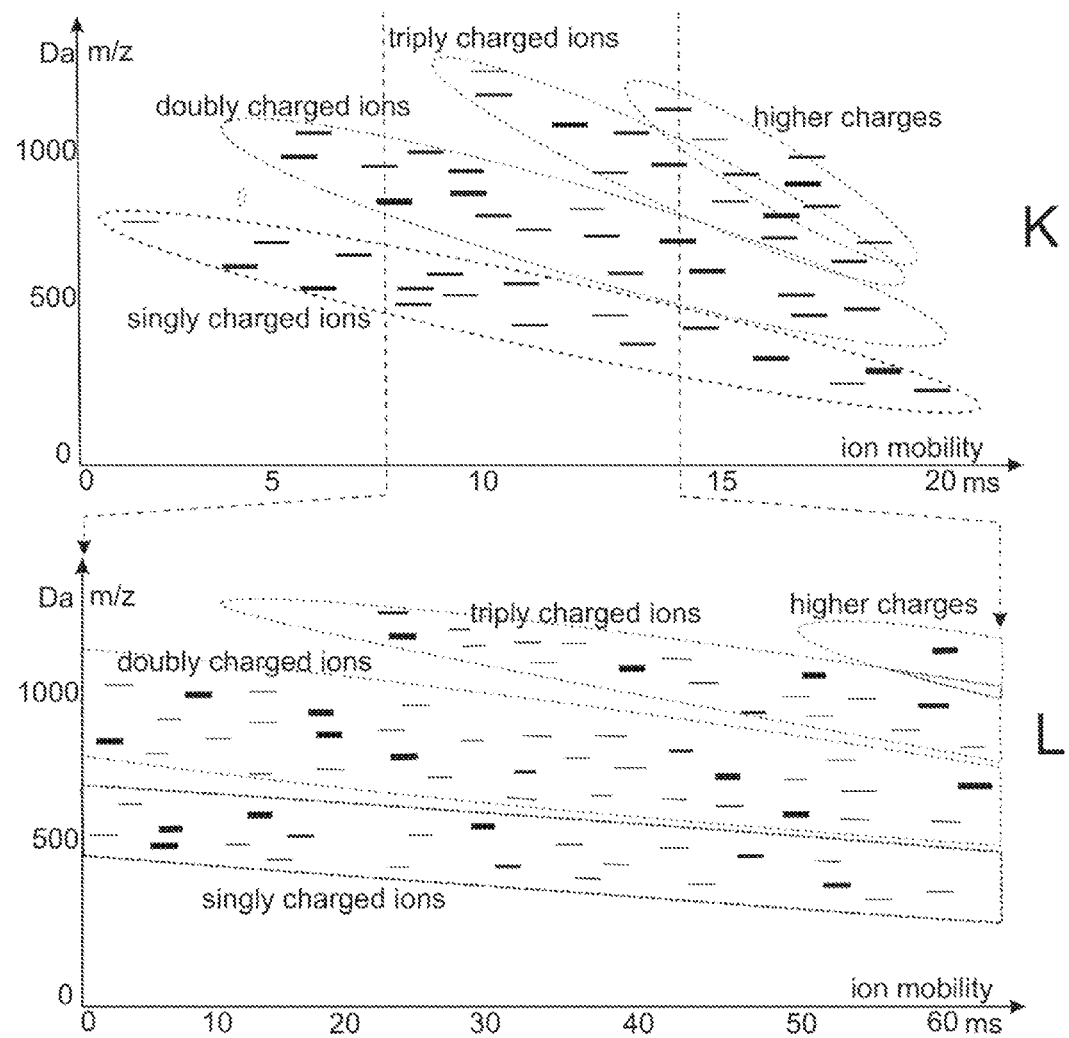
FIG. 8 presents in the upper part (K) a mass-mobility map showing the whole range of mobilities, and in the lower part (L) a mass-mobility map restricted to about ⅓ of the full mobility range using a device and a procedure according to this invention. The maps are measured using the TIMS mobility separator and the time-of-flight analyzer of the mass spectrometer of FIG. 6. The mass-mobility map (L) in the lower part is measured using method and device according to this invention, selecting only ⅓ of the full mobility range by applying correctly selected voltages to the ends of the flat ion accumulation or ion mobility scanning regions. By a three times longer accumulation of 60 milliseconds three times more ions are collected, and by an additional three times longer scan (corresponding to 180 milliseconds for the total mobility range), a mobility resolution $R_{mob} \geq 100$ is achieved. Many more ions can be detected by this procedure according to the invention.

The effect of the procedure according to the invention is shown in FIG. 8. In the upper part (K), a mass-mobility map covering the whole range of mobilities is presented, using the normal TIMS operation. A mobility resolution of about $R_{mob}$=60 is achieved by a scan time of 20 milliseconds. In the lower part (L), the mass-mobility map is restricted to about ⅓ of the full mobility range by a procedure according to this invention. The maps are measured using the TIMS mobility spectrometer and the time-of-flight analyzer of the mass spectrometer of FIG. 5. The mass-mobility map (L) in the lower part is measured using method and device according to this invention, selecting only ⅓ of the full mobility range by applying correctly selected voltages to the ends of the flat accumulation or scan regions. The flat accumulation field ramp allows for a longer accumulation time without severe losses of ions by space charge effects. By a three times longer accumulation of 60 milliseconds three times more ions are collected, and by a nine times slower scan (corresponding to 180 milliseconds for the total mobility range), a mobility resolution $R_{mob} \geq 100$ is achieved. Many more ions can be detected by this procedure according to this invention.

The zoom according to this invention will be called "spatial zoom", in contrast to the "temporal zoom" described in U.S. Pat. No. 8,766,176 B2. The zoom according to this invention spreads the ions of the mobility range of interest over almost the full lengths of the accumulation and scanning tunnels. Thereby the spatial zoom advantageously can collect considerable more ions of interest than the temporal zoom without severe losses by space charge effects, and more ions can be detected in the mass-mobility map.

Figure 9:
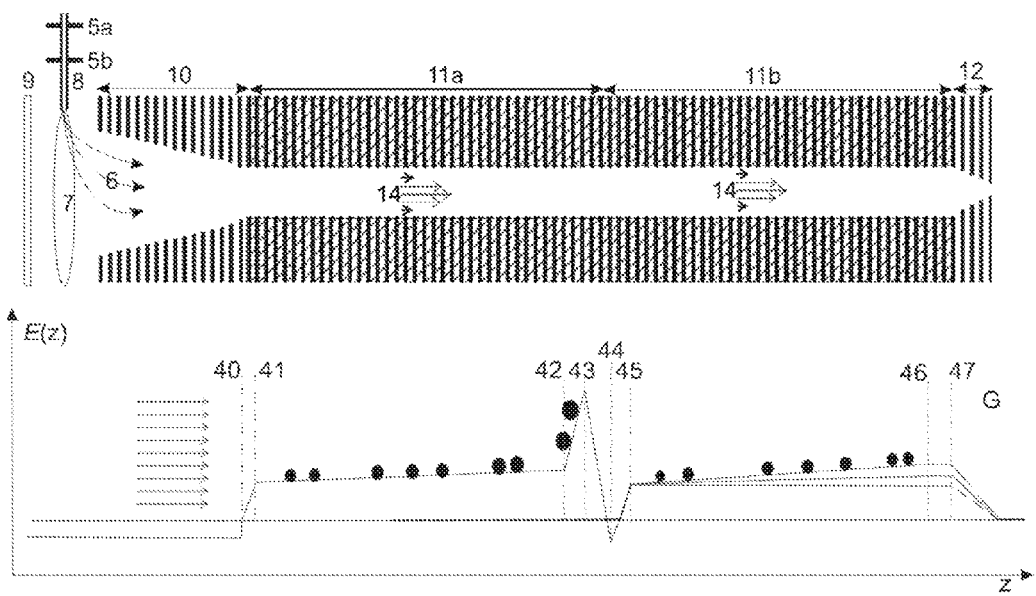
FIG. 9 illustrates a further improvement of the invention. In this figure, ions of high mobility are shown to gather in the mobility range between locations (40) and (41). These ions build up a high space charge near the axis of the device, somewhat hindering incoming ions from entering the accumulation tunnel. These ions with high mobility can be eliminated already in the inlet capillary (8) by a suitable counter-voltage between electrodes (5*a*) and (5*b*). Today, inlet capillaries with high resistance are used (see, for instance, U.S. Pat. No. 5,736,740 A, J. Franzen, 1995). If a suitable counter-field is generated within the capillary, ions with high mobility are held back and are neutralized at the highly resistive wall of the capillary.

In FIG. 7, ions of high mobility are shown to gather in the mobility range between locations (40) and (41). Although many of these ions already get lost by space charge effects, these ions build up a considerable space charge near the axis of the device, somewhat hindering incoming ions from entering the accumulation tunnel. A further improvement of the invention is given by procedures to eliminate these ions of high mobility before they enter the ion mobility spectrometer. The ions can be eliminated, for instance, by selecting the RF voltage and RF frequency in the entrance funnel (10) to not guide the ions of low masses into the ion accumulation and ion mobility scanning tunnel. A further measure is illustrated in FIG. 9. The ions with high mobilities can be eliminated already in the inlet capillary (8) by a suitable counter-voltage between electrodes (5a) and (5b). Today, inlet capillaries with high resistance are used (see, for instance, U.S. Pat. No. 5,736,740 A, J. Franzen, 1995). If a suitable counter-field is generated within the capillary, ions with high mobilities are held back and are neutralized at the highly resistive wall of the capillary.

In a further embodiment, special grids may be introduced at some positions to be able to generate sharper kinks of the electric field strength along the axis of the device. In order to keep the quadrupolar RF field intact, the grids could comprise filaments made from "leaky dielectric" material, i.e. material with very high electric resistance. Filaments with high resistance can be made by doping insulating filaments, or by using semiconductors. The filaments have a higher actual resistance for RF voltages than for DC voltages, keeping the RF quadrupole field greatly undisturbed. For the same purpose, inductive filaments may also be used, e.g. produced by winding electrically conductive material around an insulating filament.

Figure 10:
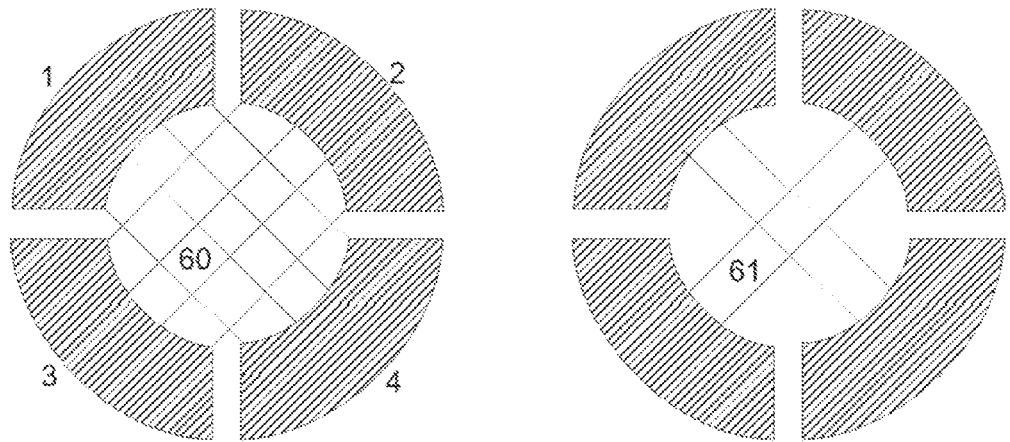
FIG. 10 illustrates electrodes with grids. The four quadrants (1) to (4), supplied with the RF voltage phases, generate the RF quadrupole field to keep the ions near the axis. The grid consists of very special filaments that do not significantly disturb the RF field, but that enable relatively sharp DC field changes on both sides of the grid. The filaments may form a leaky dielectric by a high resistance, or may show a high inductance. The grids may be used at positions (40), (41), (42), (43), (44), and (45) of profile (G) of FIGS. 7 and 9.

The grids may be very open to not hinder the gas flow. FIG. 10 presents two open grids with thin filaments. In the version on the left-hand side of the figure, four filaments each cross themselves to generate a grid which covers the cross section evenly. In the version on the right-hand side of the figure, only four filaments are used in total. Because the ions are kept very near to the axis, the small hole in the center with a diameter of only about one millimeter is sufficient to let pass the ions; on the other hand, the DC potential on the axis almost assumes the potential of the grid.

In summary, the invention proposes a trapped ion mobility spectrometer ("TIMS"), comprising RF and DC voltage generators and a stack of essentially concentric apertured electrodes, wherein an additional DC voltage is supplied to an electrode near the front of the stack to form, together with the DC voltage at electrodes near the end of the stack, a flat part of the electric field ramp, on which only ions of a selected range of mobilities are accumulated, whereby the additional DC voltage determines the highest mobility of the mobility range, and the difference between this DC voltage and the DC voltage near the end of the stack determines the width of the range between highest and lowest mobility of interest. In the trapped ion mobility spectrometer the ions of different mobilities on the flat part of the field profile can be scanned by lowering the DC voltage near the end of the stack.

Particularly, the trapped ion mobility spectrometer may additionally comprise an ion accumulation part by a further stack of electrodes and a voltage generator capable of delivering additional voltages for an electric field profile for this ion accumulation part. The voltages at the electrodes may form a flat part of the field ramp, and additional voltages form a field peak at the end of the accumulation stack of electrodes, the field peak holding back ions with lower ion mobilities than the ion mobilities of interest.

The trapped ion mobility spectrometer may comprise additional measures to keep back ions of high mobility from entering the stacks of electrodes. For instance, the ions of high mobility may be kept back within a funnel at the front of the stack of electrodes. Or the ions of high mobility may be kept back by a counter-voltage within an entrance capillary of the mass spectrometer.

The trapped ion mobility spectrometer may additionally comprise grids at some electrodes of the stack to improve the field profile. The filaments of the grids may be made from a leaky dielectric material, or the grids may comprise inductive filaments. The inductive filaments may be made by winding or depositing conductive material around thin insulation cores.

The invention also concerns a mass spectrometer, comprising a trapped ion mobility spectrometer TIMS or a TIMS with parallel ion accumulation, both equipped with additional voltage supplies according to the invention.

The capacity of the accumulation and scan units also can be increased by enlarging the whole device. A larger ion mobility spectrometer with higher RF voltages may still be acceptable for a mass spectrometer, but the gas flow, increasing with the fourth order of the inner diameter, needs to be much higher and requires more expensive vacuum pumps. This may act as a limitation for such an enlargement.

The invention claimed is:

1. A trapped ion mobility spectrometer, comprising RF and DC voltage generators and a stack of apertured electrodes, wherein an additional DC voltage supplied to an electrode near the front of the stack forms, together with a DC voltage at electrodes near the end of the stack, a flat part of an electric field ramp on which ions of a selected range of mobilities are accumulated, whereby the additional DC voltage determines the highest ion mobility of the selected range, and the difference between this DC voltage and the DC voltage near the end of the stack determines the width of the selected range.

2. The trapped ion mobility spectrometer according to claim 1, wherein the DC voltage generators are adjustable such that the accumulated ions on the flat part of the electric field ramp are scanned by lowering the DC voltage near the end of the stack.

3. The trapped ion mobility spectrometer according to claim 1, additionally comprising an ion accumulation unit having a further stack of electrodes and a voltage generator capable of delivering additional DC voltages for an electric field ramp for this accumulation unit.

4. The trapped ion mobility spectrometer according to claim 3, wherein the additional DC voltages form a flat part of the electric field ramp and an electric field peak at the end of the ion accumulation unit, such that the electric field peak holds back ions with lower mobilities than the selected range.

5. The trapped ion mobility spectrometer according to claim 1, comprising an additional measure to keep back ions of mobilities higher than the selected range from entering the stacks of electrodes.

6. The trapped ion mobility spectrometer according to claim 5, wherein the measure is an RF ion funnel at the front of the stack of aperture electrodes.

7. The trapped ion mobility spectrometer according to claim 5, wherein the measure is a counter-voltage applied to an entrance capillary of a mass spectrometer.

8. The trapped ion mobility spectrometer according to claim 1, comprising a grid at at least one of the electrodes of the stack to define the electric field profile.

9. The trapped ion mobility spectrometer according to claim 8, wherein the grid comprises filaments made from a leaky dielectric material.

10. The trapped ion mobility spectrometer according to claim 8, wherein the grid comprises inductive filaments.

11. The trapped ion mobility spectrometer according to claim 10, wherein the inductive filaments are made by winding or depositing conductive material around a thin insulation core.

12. A mass spectrometer comprising an ion source, the trapped ion mobility meter according to claim 1, and a mass analyzer wherein the trapped ion mobility spectrometer is located between the ion source and the mass analyzer.

13. A mass spectrometer comprising an ion source, the trapped ion mobility meter according to claim 4, and a mass analyzer wherein the trapped ion mobility spectrometer is located between the ion source and the mass analyzer.

* * * * *